United States Patent [19]

Widmer et al.

[11] Patent Number: 5,568,188
[45] Date of Patent: Oct. 22, 1996

[54] VIDEO ATTACHMENT TO A MICROSCOPE

[75] Inventors: Hansruedi Widmer, Niederscherli; Jurg Stucki, Oberdiessbach, both of Switzerland

[73] Assignee: Haag-Streit AG, Switzerland

[21] Appl. No.: 336,869

[22] Filed: Nov. 9, 1994

[30] Foreign Application Priority Data

May 11, 1994 [DE] Germany ............................ 9407854 U

[51] Int. Cl.$^6$ ...................................................... H04N 7/18
[52] U.S. Cl. .............................. 348/79; 348/77; 348/78; 351/236; 351/216; 351/245
[58] Field of Search .................................. 348/77, 78, 79; 351/236, 245, 216, 214; 128/633, 745

[56] References Cited

U.S. PATENT DOCUMENTS

| | | | |
|---|---|---|---|
| 4,272,161 | 6/1981 | Feinbloom | 350/320 |
| 4,883,061 | 11/1989 | Zeimer | 351/216 |
| 4,947,474 | 8/1990 | Zirm | 348/79 |
| 4,976,535 | 12/1990 | Reis | 351/216 |
| 4,987,488 | 1/1991 | Berci | 348/78 |
| 5,006,872 | 4/1991 | Parker | 348/79 |
| 5,157,428 | 10/1992 | Sklar et al. | 348/79 |
| 5,216,456 | 6/1993 | Volk | 128/633 |
| 5,216,500 | 6/1993 | Krummey et al. | 348/79 |
| 5,264,928 | 11/1993 | Howes | 348/78 |
| 5,279,296 | 1/1994 | Thurston et al. | 128/633 |
| 5,279,298 | 1/1994 | Flower | 128/633 |

OTHER PUBLICATIONS

JP 2-196208 A. In: Patents Abstracts of Japan, P-1120 Oct. 22, 1990, vol. 14/No. 484.

*Primary Examiner*—Thai Q. Tran
*Assistant Examiner*—Anano S. Rao
*Attorney, Agent, or Firm*—Ostrolenk, Faber, Gerb & Soffen, LLP

[57] ABSTRACT

The video attachment is an apparatus to be mounted laterally on a microscope and which is independent of the optic of the microscope. The apparatus comprises an imaging lens system and a video camera. The light beam path in the apparatus is deflected in such a manner that the video camera does not impede the use of the microscope. The video attachment is preferably used with a microscope of a slit lamp for the diagnosis of the eye.

10 Claims, 3 Drawing Sheets

VIDEO ATTACHMENT TO A MICROSCOPE

FIELD OF THE INVENTION

The present invention is related to a video attachment for use with a microscope. In particular, the invention is related to a video attachment for use with a microscope of a slit lamp.

SUMMARY OF THE INVENTION

In the examination of the eye, video is the ideal method for showing and recording dynamic processes such as the tearing Open of the tear film or the movement of the eyes, of the contact lenses, of the glass body, etc. In doing this, a monitor for observing or a video recorder or a computer for the recording or the storing of interesting sequences may alternatively or simultaneously be connected to a video camera. In addition to didactical applications and for documentation or illustration purposes on congresses, the video observation may also advantageously be used for the adaptation of contact lenses.

Video adapters or attachments are known. Thus, U.S. Pat. No. 4,272,161 (to Feinbloom) discloses a method of splitting a parallel beam of light indicative of the imaging of an object viewed by a microscope to enable focal registration of the image at first and second television camera locations. However, the device is complicated, heavy and voluminous; the imaging light beam is split twice in order to enable the mounting of a video tube and, on the other side, of an observer tube. Also, the user of the apparatus must remove his or her eyes from the microscope and change over to the observer tube where the eyes must be adapted anew, and, last but not least, the microscope must be modified. Such an apparatus appears not to be practical in use.

According to the Japanese publication JP-2-196208A, Patent Abstracts of Japan, P-1120, Oct. 22, 1990, Vol. 14, No. 484, a television camera is adapted onto the observing tube of a microscope. Thus, the image cannot be viewed by the observer during the recording of video images of the object to be viewed.

SUMMARY OF THE INVENTION

The first and major object of the present invention is to provide an attachment to a microscope which does not show the drawbacks of the known devices.

A second, equally important object of this invention is to provide a video adapter or attachment to a microscope which does not require any intervention in the optic of the microscope and does not impede the observer in his work with the microscope.

A third object of this invention is to provide a video adapter or attachment to a microscope which can be adapted to and removed from microscopes, even already existing microscope models.

A fourth object of this invention is to provide a video adapter or attachment to a microscope which is particularly suited for microscopes of a slit lamp.

These objects are attained by the video attachment of this invention which comprises an apparatus laterally disposed at the microscope, said apparatus having an imaging optic and comprising a video camera, said apparatus being independent of the optic of the microscope, the optical beam path being deflected within said apparatus in such a manner that the video camera does not impede the observation by the microscope.

Further objects, preferred or useful properties and characteristic of the attachment according to this invention and its other advantages will become apparent from the description of a preferred embodiment thereof with reference to the attached drawing. In particular, simple connection means are provided between the microscope and the video attachment which simultaneously serve for finely adjusting the mutual position of the microscope and the video attachment.

DETAILED DESCRIPTION OF THE INVENTION

Figure 1:
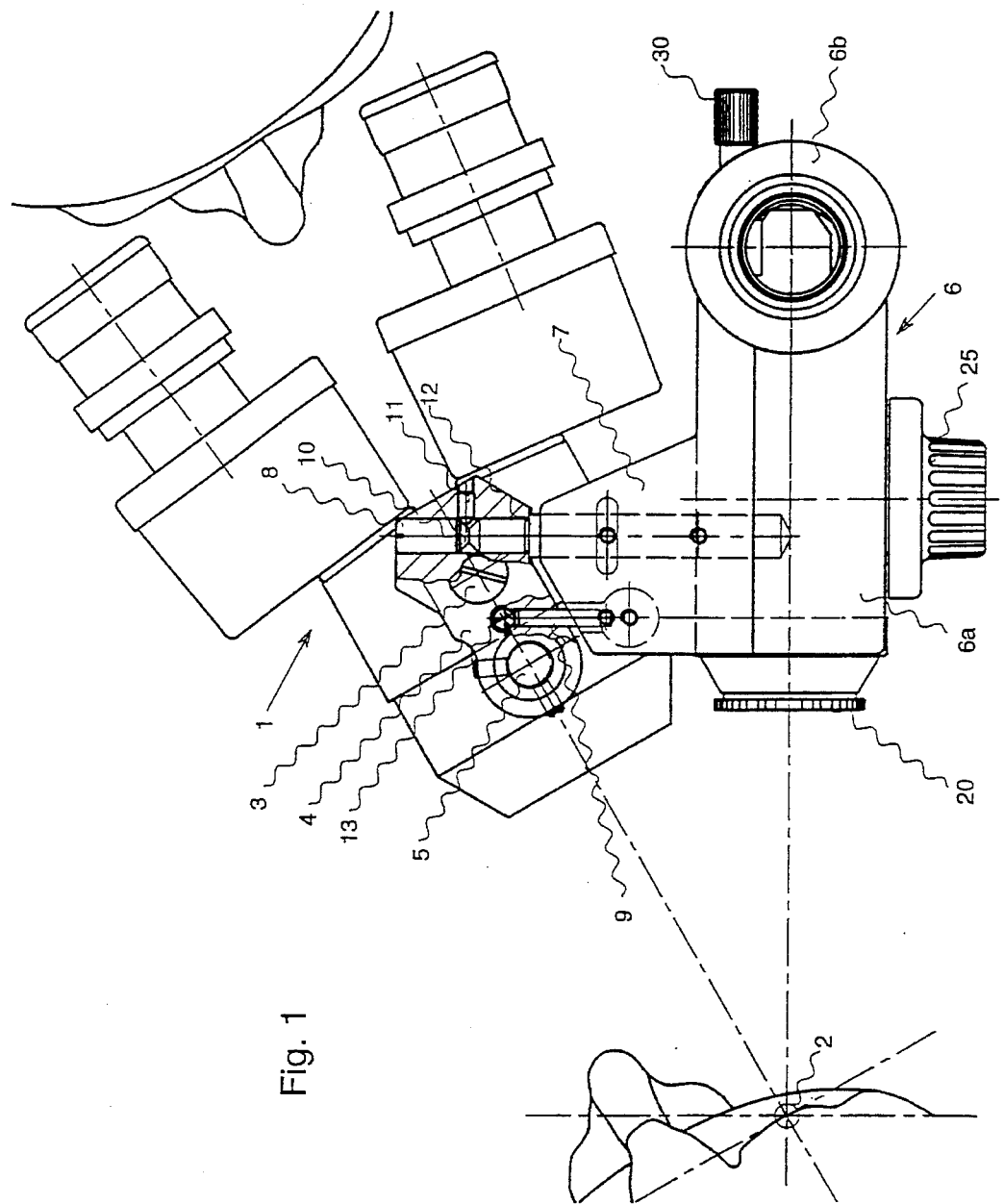
FIG. 1 shows a top view of the microscope and the video attachment adapted thereto.

FIG. 1 shows a binocular microscope 1 of conventional construction as it is currently used with slit lamps for the diagnosis of the eye. This microscope is mounted at the slit lamp on a swiveling arm which is pivotable about a vertical axis 2. During examination, the location of the eye to be observed is also brought into alignment with axis 2 as indicated in FIG. 1 by portion of a face. Also indicated in FIG. 1 is the face of an examining person which views the eye through the microscope. A base 4 is fastened to the microscope housing by means of a screw 3. A vertical peg 5, fastened in the base 4, is used for the mounting of an attachment appliance, for example a tonometer.

Figure 4:
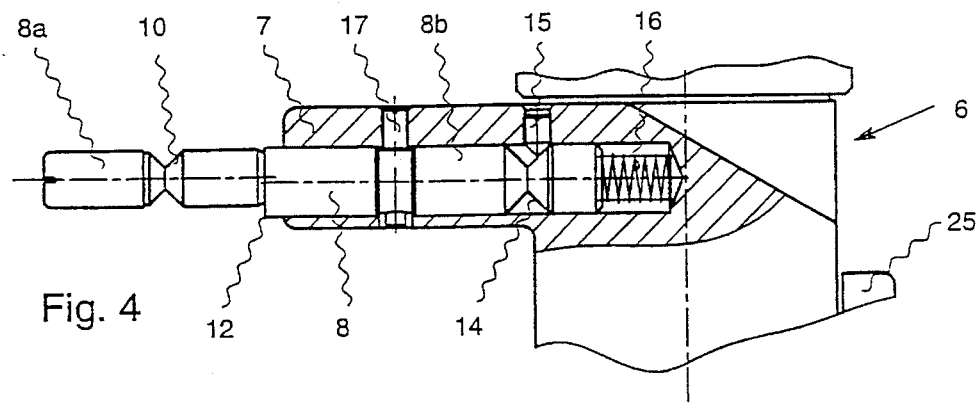
FIG. 4 shows a partial sectional view of a first fastening position of the video attachment.

A video attachment 6 is fastened laterally to the microscope 1 as an independent appliance. The housing of this video attachment has a lateral prolongation 7, see FIG. 1, which extends almost to the base 4. Two mounting tappets or pins 8 and 9 engage the prolongation 7 and also engage bores of the base 4. The tappet 8 is rotatably seated in the bores of the base 4 and of the prolongation 7, and is pulled in the mounted condition by a screw 11 engaged in a V groove 10, by means of a shoulder 12, against a stop surface of the base 4 and is thus held in a well defined axial position. The peg 9 is pressed into the base 4 against a bolt 13 which determines the penetration depth. As it is shown in FIG. 4, the peg 8 is composed of two eccentric portions 8a and 8b, each one of these two portions being situated in the base 4 and the prolongation 7 of the video attachment, respectively. The peg portion 8b comprises a further V groove 14, one of its flanks being engaged by a setting screw 15. A spring 16 maintains the peg 8 always abutted against the setting screw 15. By screwing in and screwing out of the screw 15, the axial position of the peg 8 can therefore be adjusted in both directions within the prolongation 7. A securing screw 17 serves for the fixation of the peg 8 within the prolongation 7 in a certain defined position.

Figure 5:
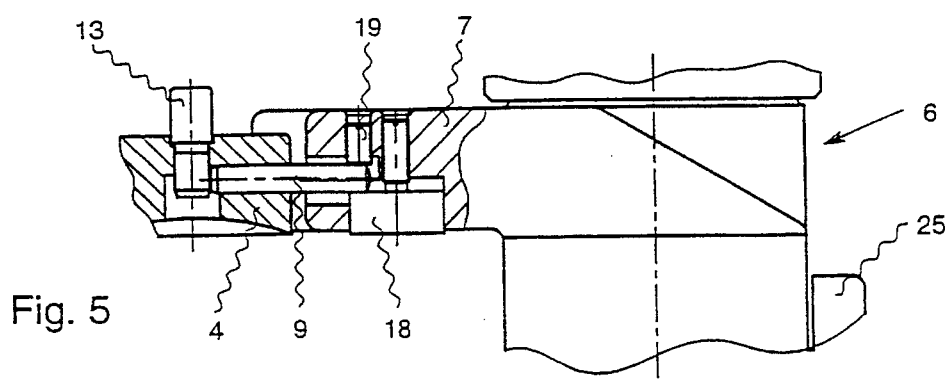
FIG. 5 shows a partial sectional view of a second fastening position of the video attachment.

According to FIG. 5, one end of the peg 9 is supported in the prolongation 7 on the head 18 of a setting screw which can be actuated from above, and it is pushed by a fixing screw 19 against the screw head 18. The fine adjusting possibilities of the mutual position between the microscope and the video attachment, provided by the conformation of the mounting pegs 8 and 9, will be explained later on.

Figure 2:
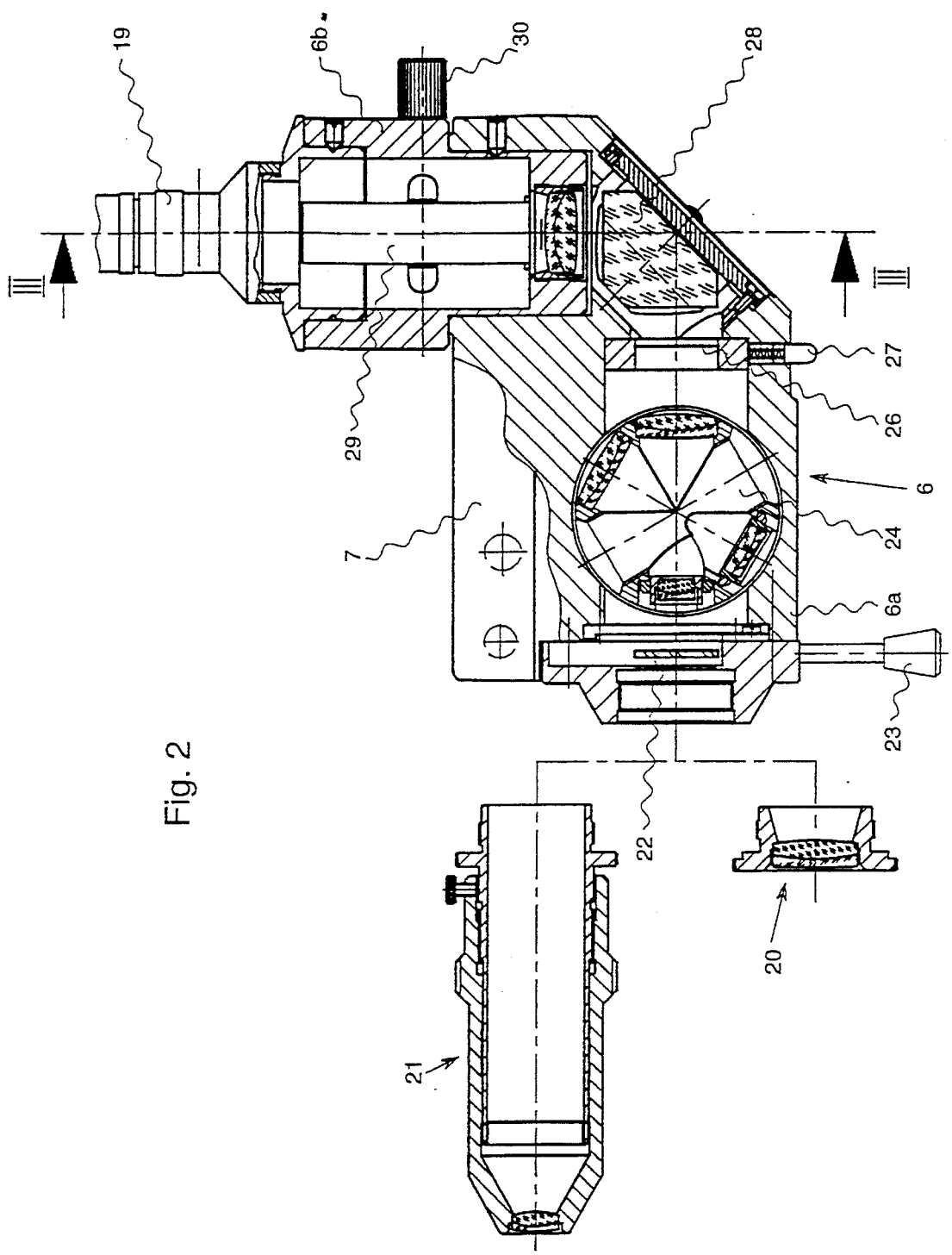
FIG. 2 shows a sectional view of the video attachment and two objectives to be mounted alternatively.
Figure 3:
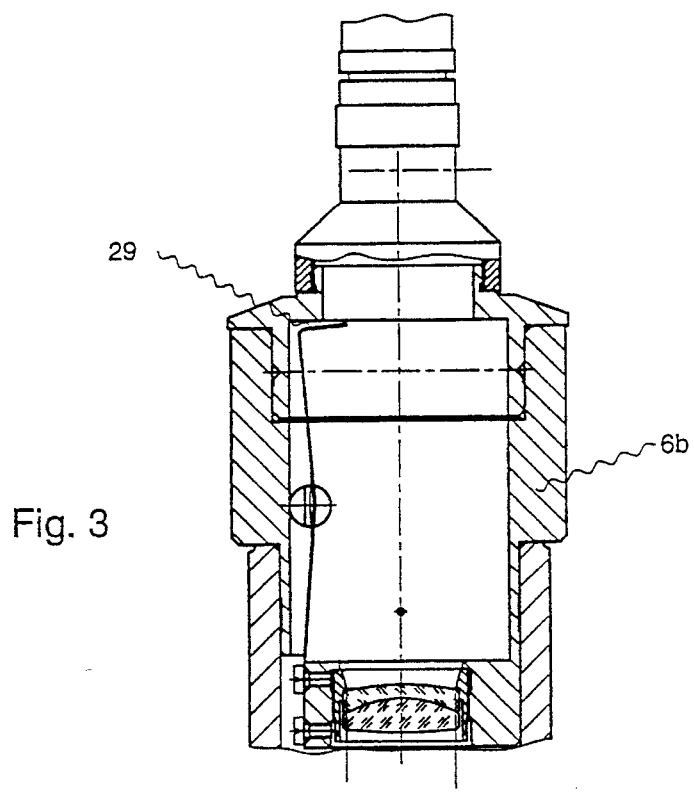
FIG. 3 shows a sectional view of a portion of the video attachment along the line III—III of FIG. 2.

FIG. 2 shows the construction of the video attachment. The housing of this attachment comprises essentially a lower portion 6a and a tube 6b on which the video camera 19 is seated. FIG. 2 shows two objectives which may be used alternatively, namely a frontal objective 20 and an endothel objective 21. A yellow filter 22 which can be inserted and removed by means of a rod assembly 23 is disposed in the housing portion 6a behind the objective. Furthermore, an objective changer 24 is provided which may be rotated by means of a turning knob 25 into the different lock-in positions. A schematically shown diaphragm 26 may be adjusted by means of a set knob 27. A prism 28 is provided for the deflection of the beam path from the horizontal optical axis to a vertical axis in the tube 6b. A frontal reflex diaphragm 29 having the shape of a flat spring which can finely be adjusted by means of a set knob 30 is disposed in this tube for masking out the frontal reflex during taking endothel images. Due to the relatively short and compact construction of this video attachment, the video camera being disposed at the top, the operation of the microscope is by no means impeded even when the video attachment is attached. Furthermore, no intervention in the optical system of the microscope is necessary. The fact that the optical axis of the video attachment encloses an angle with the optical axis of the microscope and therefore, that the image seen through the microscope will not necessarily coincide with the image recorded by the video camera, does not represent a disadvantage since a first rough adjustment of the microscope will be sufficient for a subsequent correction of the adjustment for the video recording. The recorded image may then be viewed by means of a monitor, and when the correct adjustment is reached, the desired video records can be made. These adjustments for video recording are however not effected with the aid of the above described adjusting means but by means of the fine adjusting device of the microscope or the slit lamp, respectively.

The fine adjustment of the mutual position of the microscope and the video attachment is only effected after the mounting of the video attachment. In order to get a lateral adjustment of the video attachment, the fixing screws 17 and 19 are released, and the axial position of the peg 8 within the prolongation 7 of the video attachment can be adjusted by means of the set screw 15. The video attachment is easily laterally displaceable with respect to peg 9 too. If a depth adjustment is additionally necessary in the direction of the optical axis of the video attachment, the fixing screw 11 is also slightly untightened so that the peg 8 may now be turned in its bores by means of a screwdriver. Due to the eccentricity of the peg portions 8a and 8b, the video attachment can be displaced in the direction of the optical axis with respect to the microscope. However, since this adjustment will cause a displacement in the height direction, a correction by turning the screw 18 may become necessary which readjusts the height position of the video attachment with respect to peg 9. The desired fine adjustment can be reached, if necessary step by step, whereupon the fixing screws 11, 17 and 19 are tightened in order to secure the adjusted relative position of the video attachment.

We claim:

1. A video attachment for a microscope having an optical system, comprising:

an imaging lens system, independent of the optical system of the microscope, said imaging system having a housing, means for coupling a video camera to the imaging lens system, and mounting means for mechanically fixing the imaging lens system to the microscope and for a fine adjustment between the imaging lens system and the microscope for simultaneous observation of an object by the microscope and by the imaging lens system, said mounting means including:

a mounting base fixable to said microscope, the mounting base having first and second holes, a lateral prolongation extending from the housing of said imaging lens system, the housing having third and fourth holes in alignment respectively with the first and second holes in the mounting base, a first mounting peg in the first and third holes and a second mounting peg in the third and fourth holes, the first and second mounting pegs attaching said mounting base to said housing, the first mounting peg including two eccentric parts and two V-grooves, and being rotatably and transversely movable within the first and third holes, add two screws corresponding to said V-grooves for fixing said first mounting peg in desired transverse and rotatable positions.

2. The video attachment according to claim 1, further including a prism for deflecting the optical path of said imaging lens system upwards from a horizontal plane.

3. The video attachment according to claim 1, wherein the second of mounting peg is seated on a setting screw in the mounting base and is secured by a blocking screw to the mounting base.

4. The video attachment according to claim 1, wherein the attachment further comprises a yellow filter which is insertable and removable in the attachment.

5. The video attachment according to claim 1, wherein the attachment further comprises an enlargement changer.

6. The video attachment according to claim 1, wherein the attachment further comprises an adjustable diaphragm.

7. The video attachment according to claim 1, wherein the attachment further comprises changeable objectives, including a frontal objective and an endothel objective.

8. The video attachment according to claim 1, wherein said attachment further comprises a frontal reflex mask for endothel imaging.

9. The video attachment according to claim 1, wherein the video attachment is for a microscope of the slit lamp type.

10. A combination optical and video system, comprising:

a microscope having an optical system;

a video camera;

an imaging lens system, independent of the optical system of the microscope;

means for coupling the video camera to the imaging lens system; and mounting means for mechanically fixing the imaging lens system to the microscope and for a fine adjustment between the imaging lens system and the microscope for simultaneous observation of an object by the microscope and by the imaging lens system, said mounting means including:

a mounting base fixable to said microscope, the mounting base having first and second hole, a lateral prolongation extending from the housing of said imaging lens system, the housing having third and fourth holes in alignment respectively with the first and second holes in the mounting base, a first mounting peg in the first and third holes and a second mounting peg in the third and fourth holes, the first and second mounting pegs attaching said mounting base to said housing, the first mounting peg including two eccentric parts and two V-Grooves, and being rotatably and transversely movable within the first and third holes, and two screws corresponding to said V-grooves for fixing said first mounting peg in desired transverse and rotatable positions.

\* \* \* \* \*